United States Patent
Fitch et al.

(10) Patent No.: US 9,632,072 B1
(45) Date of Patent: Apr. 25, 2017

(54) LUBRICATION CONDITION MONITORING POD FOR PRESSURIZED APPLICATIONS

(71) Applicant: Luneta, LLC, Tulsa, OK (US)

(72) Inventors: James Chester Fitch, Tulsa, OK (US); Thomas Chester Fitch, Tulsa, OK (US)

(73) Assignee: Luneta, LLC, Tulsa, OK (US)

( * ) Notice: Subject to any disclaimer, the term of this patent is extended or adjusted under 35 U.S.C. 154(b) by 186 days.

(21) Appl. No.: 14/689,835

(22) Filed: Apr. 17, 2015

Related U.S. Application Data (60) Provisional application No. 61/981,551, filed on Apr. 18, 2014.

(51) Int. Cl.
*G01N 33/26* (2006.01)

(52) U.S. Cl.
CPC .................... *G01N 33/26* (2013.01)

(58) Field of Classification Search
CPC .... G01N 33/26; G01N 1/08; G01N 2001/205; A61B 17/00491; A61B 17/0057; A61B 17/12022
See application file for complete search history.

(56) References Cited

U.S. PATENT DOCUMENTS

| | | | |
|---|---|---|---|
| 2,830,261 A * | 4/1958 | Estelle | G01N 27/07 137/560 |
| 3,923,657 A | 12/1975 | Roser | |
| 4,262,533 A * | 4/1981 | Jaeger | G01N 1/2035 73/863.11 |
| 4,468,613 A | 8/1984 | Slough et al. | |
| 4,537,071 A * | 8/1985 | Waterman | B25B 27/143 73/866.5 |
| 4,557,216 A | 12/1985 | Demyon | |
| 4,615,413 A | 10/1986 | Stevenson | |
| 4,827,770 A | 5/1989 | Schwartz et al. | |
| 4,888,990 A | 12/1989 | Bryan et al. | |
| 4,993,460 A | 2/1991 | Robinson et al. | |
| 5,243,929 A | 9/1993 | Brown et al. | |
| 5,628,231 A | 5/1997 | Sheridan | |
| 6,082,972 A | 7/2000 | Moore, Jr. et al. | |

(Continued)

OTHER PUBLICATIONS

International Search Report and Written Opinion for Application PCT/US2014/032542 mailed Dec. 16, 2014.

(Continued)

*Primary Examiner* — Francis Gray
(74) *Attorney, Agent, or Firm* — Dunlap Codding, P.C.

(57) ABSTRACT

A machine fluid testing probe is disclosed having a handle, a shaft connected to the handle, and a plurality of indicators supported by the shaft. The shaft has a first end, a second end opposite the first end, a first portion extending from the first end toward the second end, a second portion extending from the first portion toward the second end, and a shoulder defined by the second portion. The second portion has a continuous arcuate external surface having a second cross-sectional axis greater than a first cross-sectional axis of the first portion. The shaft is configured to contact a machine fluid. The plurality of indicators are supported by the first portion of the shaft between the first end and the second end. Each of the plurality of indicators is configured to test for one or more contaminants in the machine fluid.

36 Claims, 7 Drawing Sheets

(56) References Cited

U.S. PATENT DOCUMENTS

| | | | |
|---|---|---|---|
| 6,546,819 B1* | 4/2003 | Schadt | G01N 1/14 |
| | | | 137/423 |
| 7,788,973 B2 | 9/2010 | Quill | |
| 8,316,653 B2 | 11/2012 | Appler et al. | |
| 2003/0188588 A1* | 10/2003 | Jaeger | G01N 1/2035 |
| | | | 73/863.84 |
| 2010/0107496 A1 | 5/2010 | Faria | |
| 2010/0269584 A1 | 10/2010 | Horst | |
| 2014/0311240 A1 | 10/2014 | Fitch et al. | |

OTHER PUBLICATIONS

KIPP—Dome oil level sight glasses; http://www.kipp.com/cl/en/Products/Operating-parts-standard-elements/Level-indicators-Screw-plugs/pid.1097.1226/agid.13228.1842/ecm.ag/Dome-oil-le, Nov. 21, 2014.

Trico Corp Viewport 3D Plastic Lens, http://www.tricocorp.com/product/viewports-3d-plastic-lens, Nov. 21, 2014.

3D Bullseye, 3D Bullseye Oil Sight Glass-3D Oil Level Glass Esco Products, http://www.escopro.com/oil-sight-glass/3d-bulls-eye.html, Nov. 20, 2014.

Horizontal Oil Sight Glass, Horizontal Oil Sight Glass-Horizontal Oil Sight Glass-Oil Sight Glass Product Line, Esco Products, http://www.escopro.com/oil-sight-glass/horizontal-esco-oil-signt-glass/horizontl-oil-sight-glass.html, Nov. 20, 2014.

Sight Glass W/O-Ring, Sight Glass W/O-Ring [33-RG-001]—$6.99: Midwest Bus Parts, We do More than Bus Parts, http://www.midwestbusparts.com/index.php?main_page=product_infor&cPath-25_715&products_id=32998&zenid-fgunfjhrmlohvmiec8d9oe71i2, Nov. 21, 2014.

Sump Bottles, BS&W Bowl-Trico Corp., http://www.tricocorp.com/product/sump-bottles/, Nov. 20, 2014.

* cited by examiner

LUBRICATION CONDITION MONITORING POD FOR PRESSURIZED APPLICATIONS

INCORPORATION BY REFERENCE/CROSS-REFERENCE

The present patent application claims priority to U.S. Ser. No. 61/981,551, filed on Apr. 18, 2014, the entire content of which is hereby incorporated herein by reference.

BACKGROUND

Most machines used in manufacturing and other industries require machine fluids for lubrication and function of machine components. Exemplary machine fluids include lubricants and oils which may be based upon hydrocarbons, synthetic, and/or petroleum based products. Other types of machine fluids include hydraulic fluids. The machine fluids typically must be maintained within a preferred range of composition for cleanliness for efficient performance of the machine. For example, when oil is used as a machine fluid, the unwanted addition of water or debris may cause the machine to loose efficiency or sustain damage.

In the past, machine fluids were monitored through the collection and analysis of samples of the machine fluid. However, some current sampling and monitoring processes are inefficient, time consuming, and costly. For example, sampling may be taken from the bottom of the sump of machines (e.g., from drain ports), which can mix the lubricant with sediment making effective oil monitoring difficult. Sample may also require that the machine be stopped or even drained of lubricant, causing a loss of production of the machine. The best sample location and device enables the lubricant to be sampled from moving (representative) fluid without temporary loss of production. Therefore, an apparatus is needed to more efficiently monitor (through onsite inspection techniques) and sample machine fluids from a single location.

SUMMARY

In one embodiment, a machine fluid testing assembly is disclosed. The machine fluid testing assembly has a sight glass, a probe extending through the sight glass, and at least one seal surrounding the probe. The sight glass is at least partially constructed of one or more material that is transparent to light in a visible region. The sight glass is configured to be attachable to a machine such that machine fluid is viewable through the sight glass. The sight glass has an inside surface surrounding a cavity, an outside surface, and a bore extending from the inside surface to the outside surface. The probe extends through the bore of the sight glass such that at least a portion of the probe is positionable for contact with the machine fluid. The probe has a handle, a shaft extending outwardly from the handle, a stop member connected to the shaft, and a plurality of indicators positioned on the shaft. The shaft has a first end proximate to the handle, a second end opposite the first end, and a length extending between the first end and the second end. The shaft is configured to be removably extended into the cavity to contact a machine fluid within the cavity. The stop member is connected to the shaft, proximate to the second end and extends outwardly from the shaft to prevent removal from the cavity. The plurality of indicators are positioned on the shaft to contact the machine fluid and are configured to test for one or more contaminants within the machine fluid. The least one seal surrounds the bore and extends into the bore to engage the shaft to prevent the machine fluid from exiting the bore.

In another version, a machine fluid testing probe is disclosed. The machine fluid testing probe has a handle, a shaft connected to the handle, and a plurality of indicators supported by the shaft. The shaft is connected to the handle and extends outwardly from handle. The shaft has a first end proximate to the handle, a second end opposite the first end, and a length extending between the first end and the second end, a first portion extending from the first end toward the second end, a second portion extending from the first portion toward the second end, and a shoulder defined by the second portion of the shaft at an intersection of the first portion and the second portion. The first portion has a first cross-sectional axis. The second portion has a continuous arcuate external surface having a second cross-sectional axis greater than the first cross-sectional axis and extending across the continuous arcuate external surface. The shaft is configured to be removably positioned to contact a machine fluid of a machine. The plurality of indicators are supported by the first portion of the shaft between the first end and the second end so as to contact the machine fluid. Each of the plurality of indicators is configured to test for one or more contaminants in the machine fluid. A first indicator of the plurality of indicators has at least a first indicator cross-sectional axis which is smaller than the second cross-sectional axis of the second portion of the shaft whereby the first indicator at least partially defines a recess.

In another embodiment, a machine fluid testing assembly is disclosed. The machine fluid testing assembly has a handle, a shaft connected to the handle, a plurality of indicators supported by the shaft, and a coupling body in which the shaft is positionable. The shaft is connected to the handle and extends outwardly from the handle. The shaft has a first end proximate to the handle, a second end opposite the first end, and a length extending between the first end and the second end, a first portion extending from the first end toward the second end, a second portion extending from the first portion toward the second end, and a shoulder defined by the second portion of the shaft at an intersection of the first portion and the second portion. The first portion has a first cross-sectional axis. The second portion has a continuous arcuate external surface having a second cross-sectional axis greater than the first cross-sectional axis and extending across the continuous arcuate external surface. The shaft is configured to be removably positioned to contact a machine fluid of a machine. The plurality of indicators is supported by the first portion of the shaft between the first end and the second end so as to contact the machine fluid. Each of the plurality of indicators is configured to test for one or more contaminants in the machine fluid. A first indicator of the plurality of indicators has at least a first indicator cross-sectional axis which is smaller than the second cross-sectional axis of the second portion of the shaft whereby the first indicator at least partially defines a recess. The coupling body has an open first end and an open second end, an inside surface and an outside surface extending from the open first end to the open second end forming a coupling body cavity such that the shaft is positionable within the coupling body cavity. The coupling body further has a port extending from the coupling body cavity through the inside surface and the outside surface.

BRIEF DESCRIPTION OF THE DRAWINGS

Certain embodiments of the inventive concepts will hereafter be described with reference to the accompanying drawings, wherein like reference numerals denote like elements. It should be understood, however, that the accompanying figures illustrate the various implementations described herein and are not meant to limit the scope of the various technologies described herein.

DETAILED DESCRIPTION

Specific embodiments of the inventive concepts disclosed herein will now be described in detail with reference to the accompanying drawings. Further, in the following detailed description of embodiments of the present disclosure, numerous specific details are set forth in order to provide a more thorough understanding of the disclosure. However, it will be apparent to one of ordinary skill in the art that the embodiments disclosed herein may be practiced without these specific details. In other instances, well-known features have not been described in detail to avoid unnecessarily complicating the description.

Unless expressly stated to the contrary, "or" refers to an inclusive or and not to an exclusive or. For example, a condition A or B is satisfied by anyone of the following: A is true (or present) and B is false (or not present), A is false (or not present) and B is true (or present), and both A and B are true (or present).

In addition, use of the "a" or "an" are employed to describe elements and components of the embodiments herein. This is done merely for convenience and to give a general sense of the inventive concept. This description should be read to include one or at least one and the singular also includes the plural unless otherwise stated.

The terminology and phraseology used herein is for descriptive purposes and should not be construed as limiting in scope. Language such as "including," "comprising," "having," "containing," or "involving," and variations thereof, is intended to be broad and encompass the subject matter listed thereafter, equivalents, and additional subject matter not recited or inherently present therein.

As used herein any references to "one embodiment," "an embodiment," or "some embodiments" means that a particular element, feature, structure, or characteristic described in connection with the embodiment is included in at least one embodiment. The appearances of the phrase "in one embodiment" in various places in the specification may not refer to the same embodiment.

Figure 1:
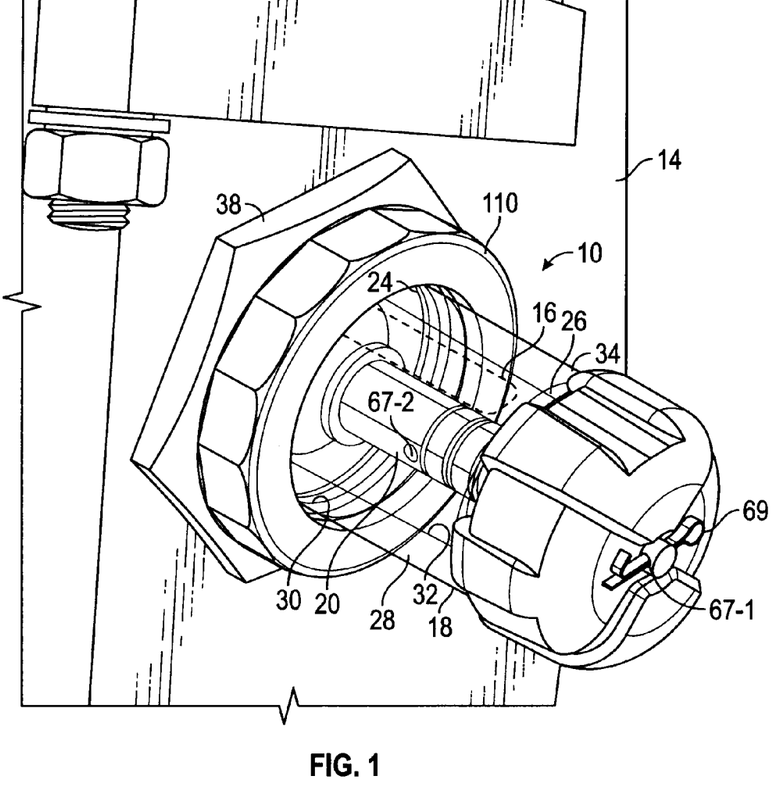
FIG. 1 is a perspective view of a machine fluid testing assembly, in accordance with some embodiments of the present disclosure.
Figure 2:
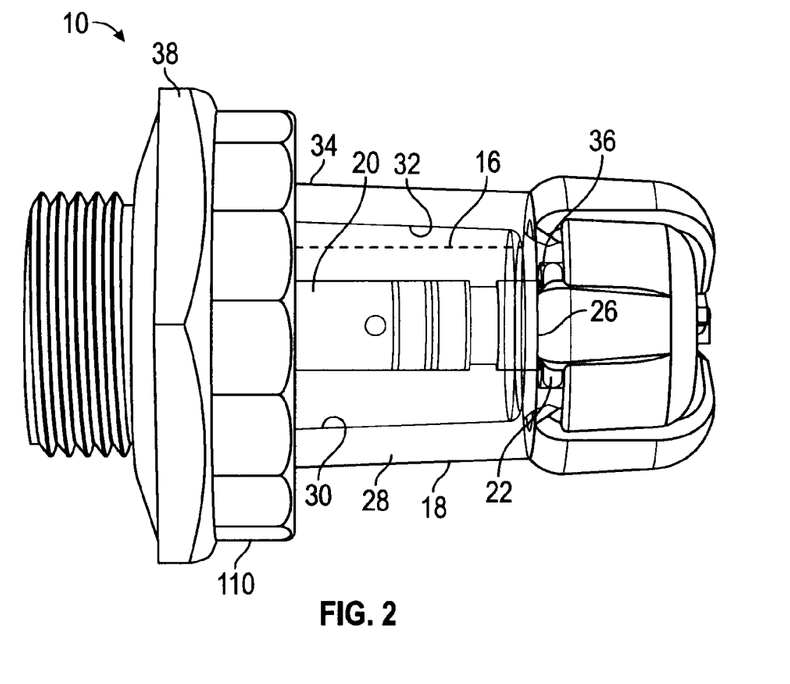
FIG. 2 is a side view of the machine fluid testing assembly of FIG. 1.

Referring now to FIGS. 1 and 2, therein shown is a machine fluid testing assembly 10 mounted to a machine 14 in accordance with the present disclosure such that a machine fluid 16 (shown in phantom) within the machine 14 enters into a sight glass 18 of the machine fluid testing assembly 10. The machine fluid testing assembly 10 may be mounted onto the machine 14 at a location below the machine fluid 16 level within the machine 14. Thus, the sight glass 18 will be filled with the machine fluid 16. Also, the machine fluid 16 may need to be under pressure in a range from 30-100 PSI above atmospheric pressure. For this reason, the machine fluid testing assembly 10 is designed to seal against and maintain pressure within the machine 14.

Figure 4:
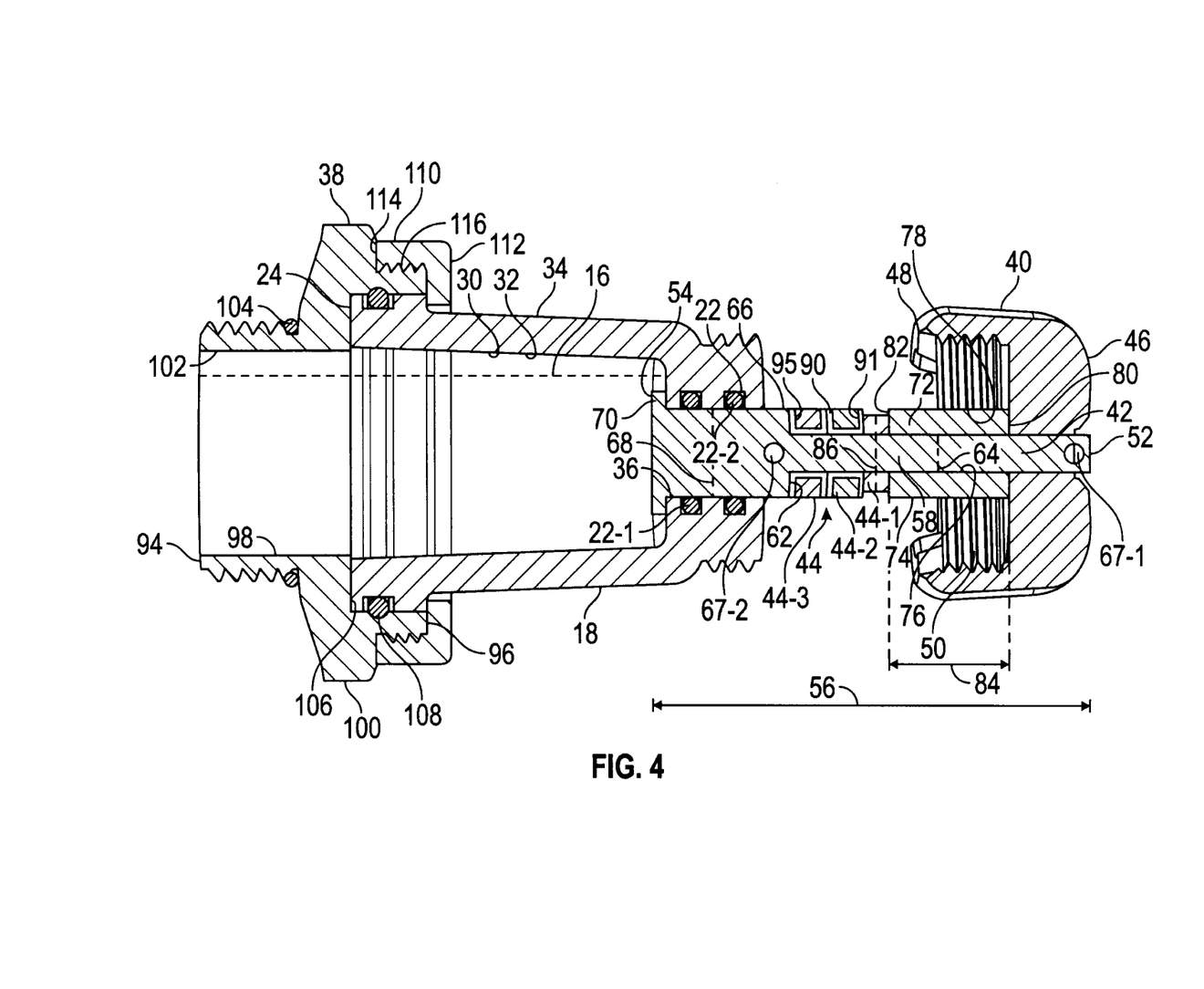
FIG. 4 is a cross sectional view of the machine fluid testing assembly of FIG. 3, taken along line 4-4 of FIG. 3.

The machine fluid testing assembly 10 may include the sight glass 18, a machine fluid testing probe 20 extending through the sight glass 18, and at least one seal 22 (see FIG. 4). The sight glass 18 may be at least partially constructed of one or more material that is transparent to light in a visible region, such that the machine fluid 16 is visible to a person monitoring the condition of the machine fluid 16. The sight glass 18 may be configured to be attachable to a machine 14 such that machine fluid 16 is viewable through the sight glass 18. In some embodiments, the sight glass 18 may be constructed, at least in part, from glass; borosilicate glass; plastics, such as polytetrafluoroethylene, polyethylene terephthalate (PET), polyvinyl chloride (PVC), polyethylene (PE), polybutylene terephthalate (PBT); or other suitable materials which are transparent to light in the visible region of the light spectrum. The sight glass 18 may be formed by moulding, injection moulding, blowing, machining, 3D printing, a combination thereof, or any other suitable method.

In some embodiments, as shown in FIG. 4, the sight glass 18 may have an open first end 24, an open second end 26 opposite the open first end 24 and spaced a distance therefrom, and a sidewall 28 extending between the open first end 24 and the open second end 26. The sight glass 18 may have an inside surface 30 surrounding a cavity 32, an outside surface 34, and a bore 36 extending from the inside surface 30 to the outside surface 34. In some embodiments, the inside surface 30 and the outside surface 34 may be an inside surface and an outside surface of the sidewall 28. Further, in some embodiments, the open second end 26 may define the bore 36 although the bore 36 can be positioned in another location.

In some embodiments, the open first end 24 of the sight glass 18 may be configured to be releasably attachable to the machine 14 directly or indirectly such that the machine fluid 16 is transferrable from the machine 14 to the sight glass 18. For example, the open first end 24 of the sight glass 18 may be configured to be releasably attachable to the machine 14 directly via a threaded connection, one or more clamp, one or more nut and bolt assembly, or any other suitable releasable attachment mechanism. By way of another example, as shown in FIGS. 1 and 2, the open first end 24 of the sight glass 18 may be configured to be releasably attached to the machine 14 indirectly via a coupling body 38, described in more detail below. In either event, the sight glass 18 may be releasably connected to the machine without destruction of the machine 14 or the sight glass 18.

Figure 3:
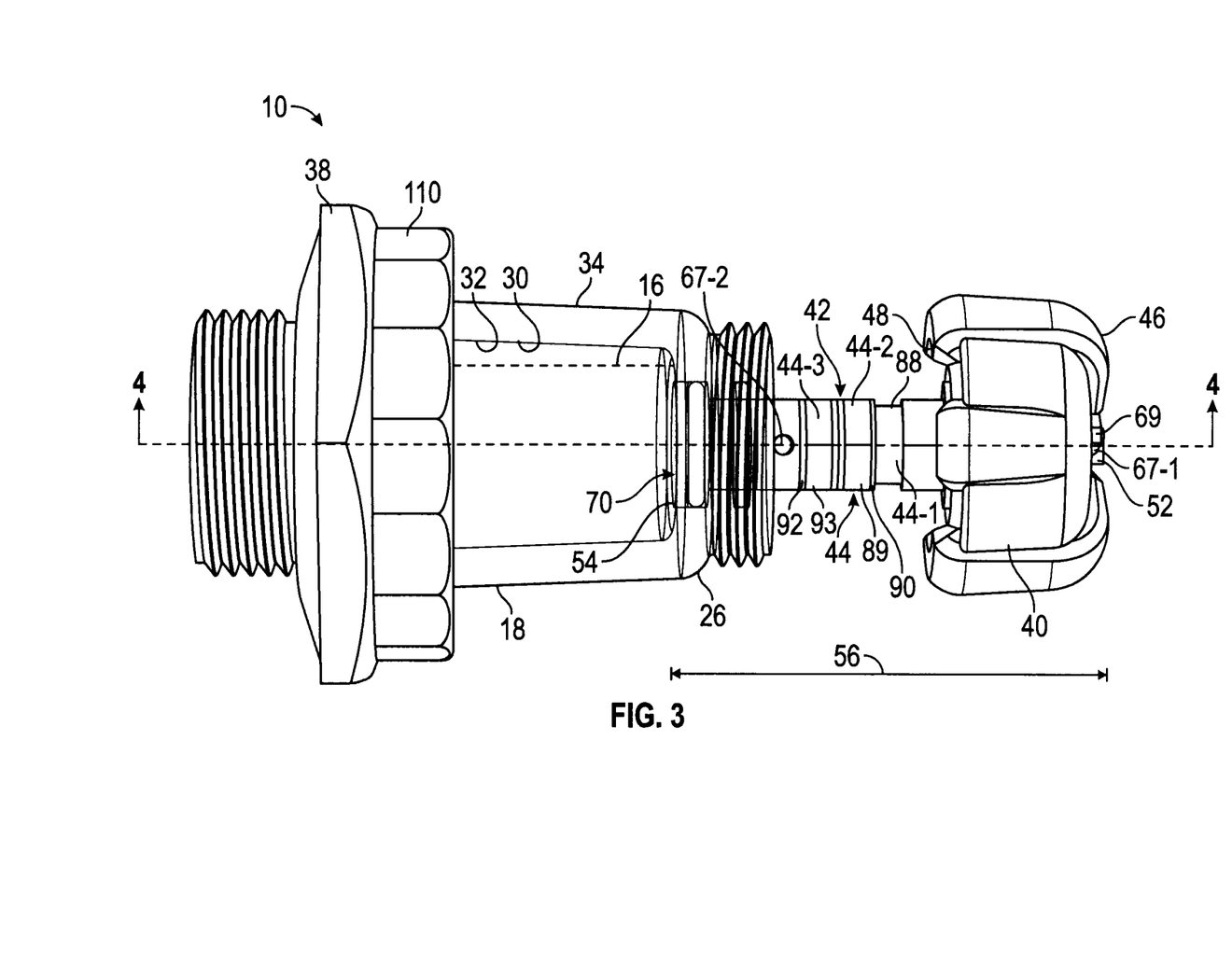
FIG. 3 is a side view of the machine fluid testing assembly with a machine fluid testing probe in an extended position, in accordance with some embodiments of the present disclosure.
Figure 5:
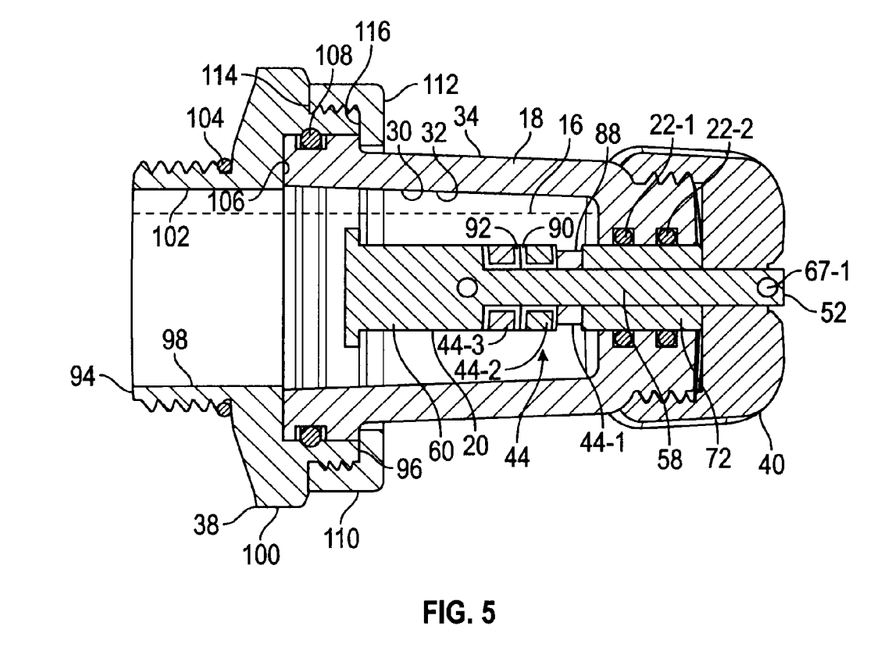
FIG. 5 is a cross sectional view of the machine fluid testing assembly with the machine fluid testing probe in a collapsed position, in accordance with some embodiments of the present disclosure.

Referring now to FIGS. 3-5, therein shown is the machine fluid testing assembly 10 and the machine fluid testing probe 20, also hereinafter referred to as "the probe 20". The probe 20 may extend through the bore 36 of the sight glass 18 such that at least a portion of the probe 20 is positionable for contact with the machine fluid 16. In some embodiments, the probe 20 may include a handle 40, a shaft 42 extending outwardly from the handle 40, and a plurality of indicators 44 positioned on the shaft 42.

The handle 40 may have a first end 46 and a second end 48 opposite the first end 46. The second end 48 of the handle 40 may be shaped to form a recess 50 extending inwardly toward the first end 46. In some embodiments, the shaft 42 may be releasably connected to the handle 40 without destruction of the shaft 42 or the handle 40, as will be explained in more detail below. The handle 40 may be configured to be releasably connected to the sight glass 18. For example, in some embodiments, as shown in FIGS. 4 and 5, the handle 40, adjacent to the recess 50 may be threaded to engage a cooperating threading proximate to the open second end of 26 of the sight glass 18. In some other embodiments, the handle 40 may be releasably connected to the sight glass 18 via a snap fit connection, a pinned connection, a clamp member, a set screw, a nut and bolt assembly, or any other suitable connection method. The handle 40 may be formed from metals, such as aluminium, steel, or stainless steel; plastics, such as polytetrafluoroethylene, PET, PVC, PE, PBT; or any other suitable material. The handle 40 may be formed by casting, forging, machining, moulding, injection moulding, 3D printing, sintering, 3D sintering, or any other suitable method.

The shaft 42 may be configured to be removably extended into the cavity 32 to contact the machine fluid 16 within the cavity 32. The shaft 42 may be connected to the handle 40 and extend outwardly from the handle 40. For example, as shown in FIGS. 4 and 5, the shaft 42 may be positioned within and extend outwardly from the recess 50 of the handle 40. The shaft 42 may include a first end 52 proximate to the handle 40, a second end 54 opposite the first end 52, and a length 56 extending between the first end 52 and the second end 54. The length 56 may be sufficient to enable the plurality of indicators 44 to contact the machine fluid 16 when the shaft 42 is positioned within the cavity 32 of the sight glass 18 and be removed from the cavity 32 to be exposed to the atmosphere. In some embodiments, the shaft 42 may further include a first portion 58 extending from the first end 52 toward the second end 54, a second portion 60 extending from the first portion 58 toward the second end 54, and a shoulder 62 defined by the second portion 60 of the shaft 42 at an intersection of the first portion 58 and the second portion 60. In some embodiments, at least a portion of the shaft 42 may be formed with a circular cross section, an elliptic cross section, or any other cross section suitable to enable the seal 22 surrounding the bore 36 to engage at least a portion of the shaft 42 to prevent the pressurized machine fluid 16 from exiting the bore 36 when the probe 20 is at least partially removed from within the cavity 32 of the sight glass 18. In some embodiments, the second portion 60 has a cylindrical configuration.

The shaft 42 may be constructed from metals, such as aluminium or stainless steel; plastics, such as polytetrafluoroethylene, PET, PVC, PE, PBT; or any other suitable material. In some embodiments, the shaft 42 may be constructed from materials which are inert or substantially inert to the machine fluid 16, contaminants within the machine fluid 16, or a combination of the machine fluid 16 and possible contaminants contained within the machine fluid 16. The shaft 42 may be formed by casting, forging, machining, moulding, injection moulding, 3D printing, sintering, 3D sintering, or any other suitable method.

The first portion 58 may have a first cross-sectional axis 64 extending across first portion 58. For example, in embodiments where the first portion 58 of the shaft 42 has a circular cross section, the first cross-sectional axis 64 may extend along the diameter of the circular cross-section. By way of another example, in some embodiments where the first portion 58 of the shaft 42 has an elliptic (or other) cross-section, the first cross-sectional axis 64 may extend along either a major axis (transverse diameter) or a minor axis (conjugate diameter) of the elliptic cross-section. In some embodiments, the first portion 58 may have a polygonal cross section, such as a square, a rectangular, triangular, a hexagonal, or other cross section, for example.

In some embodiments, the first portion 58 of the shaft 42 may include a connection mechanism proximate to the first end 52 to releasably connect the shaft 42 to the handle 40. For example, in some embodiments, as shown in FIGS. 1 and 3-5, the first portion 58 of the shaft 42 may define a hole 67-1 proximate to the first end 52 of the shaft 42. The hole 67-1 may be configured to receive a cotter pin 69 to secure the handle 40 to the shaft 42. It should be understood to one skilled in the art that, although shown with the hole 67-1 and the cotter pin 69, the connection mechanism of the first end 58 of the shaft 42 may be any suitable connection mechanism, such as cooperating threaded sections on the first portion 58 and the handle 40, a friction fit connection, a clip connection, a clamp connection, a set screw, a pin and detent, or any other suitable connection mechanism.

In some embodiments, the second portion 60 may have a continuous arcuate external surface 66 having a second cross-sectional axis 68 greater than the first cross-sectional axis 64 and extending across the continuous arcuate external surface 66. In some embodiment, the continuous arcuate external surface 66 of the second portion 60 of the shaft 42 may be circular, elliptic, or any other continuous arcuate shape. Similar to the first portion 58, when the continuous arcuate external surface 66 of the second portion 60 is circular, the second cross-sectional axis 68 may extend along the diameter of the circular cross-section. Where the continuous arcuate external surface 66 is elliptic, the second cross-sectional axis 68 may extend along a major axis or a minor axis of the second portion 60.

In some embodiments, the second portion 60 may include a securing mechanism for securing the probe 20 in an extended position for visual inspection of the plurality of indicators 44. For example, as shown in FIGS. 1 and 3-5, the second portion 60 may define a hole 67-2 configured to enable insertion of a cross brace (not shown) securing the probe 20 during inspection of the plurality of indicators 44. The hole 67-2 may be positioned on the second portion 60 so as to enable a cross brace to be inserted at least partially into the hole 67-2 and enable the cross brace to contact the open second end 26 of the sight glass 18 to prevent the probe 20 from being re-inserted into the cavity 32 during inspection. Although shown as the hole 67-2 and cross brace cooperating to form the securing mechanism, it should be known to one skilled in the art that the securing mechanism may be any suitable securing mechanism, such as a clamp, a clip, a friction fit, an collapsible brace extendable from within the shaft 42, a nut and bolt assembly, a set screw, or any other suitable securing mechanism.

The shoulder 62, formed by the second portion 60 of the shaft 42 at the intersection of the first portion 58 and the second portion 60 of the shaft, may extend a distance outwardly from a surface of the first portion 58 to the continuous arcuate external surface 66 of the second portion 60. In some embodiments, the shoulder 62 may be configured to contact one of the plurality of indicators 44 so as to aid in positioning the plurality of indicators 44 along the shaft 42. The shoulder 62 may also act as a surface against which one of the plurality of indicators 44 may be secured to prevent the plurality of indicators 44 from moving when positioned on the shaft 42.

In some embodiments, a stop member 70 may be connected to the shaft 42, proximate to the second end 54 of the shaft 42. The stop member 70 may extend outwardly from the shaft 42 to prevent removal of the shaft 42 from the cavity 32 of the sight glass 18. For example, the stop member 70 may have a cross-sectional axis greater than the second cross-sectional axis 68 of the second portion 60 of the shaft 42. In some embodiments, the stop member 70 may be connected to the shaft 42 by a set screw, a nut and bolt assembly, a threaded section of the stop member 70 cooperating with a threaded section of the shaft 42, brazing, welding, or any other suitable connection mechanism. In some embodiments, the stop member 70 may be integral to the shaft 42 and formed contemporaneously with the shaft 42. In these embodiments, where the stop member 70 is integral to the shaft 42, the stop member 70 may form a third portion 71 between the second end 54 and the second portion 60 of the shaft 42, where the third portion 71 extends outwardly relative to the continuous arcuate external surface 66 of the second portion 60. In either event, the cross-sectional axis of the stop member 70 may be larger than the size of the bore 36, such that when the probe 20 is at least partially removed from the sight glass 18, the outward movement of the probe 20 may be limited when the stop member 70 contacts the inside surface 30 of the sight glass 18 proximate to the open second end 26.

In some embodiments, the probe 20 may include a spacer 72 supported by the first portion 58 of the shaft 42 and positioned between the plurality of indicators 44 and the handle 40. The spacer 72 may have a uniform cross-sectional axis equal to the second cross-sectional axis 68 of the second portion 60 of the shaft 42, such that outer surfaces of the spacer 72 and the second portion 60 are co-extensive to maintain contact with the seal 22 during removal and insertion of the probe 20 into the cavity 32. In some embodiments, the spacer 72 may be configured as a tube with an exterior surface 74, an interior surface 76 defining a receiving passage 78, a first end 80, a second end 82, and a length 84 extending between the first end 80 and the second end 82. The receiving passage 78 may be configured to matingly receive the first portion 58 of the shaft 42. The first end 80 may be configured to contact the handle and the second end 82 may be configured to contact one of the plurality of indicators 44. In this embodiment, the length 84 may be sufficient to cause the spacer 72 to secure the plurality of indicators 44 between the shoulder 62 and the second end 82 of the spacer 72 when the handle 40 is connected to the shaft 42 and contacting the first end 80 of the spacer 72.

The plurality of indicators 44 may be supported by the first portion 58 of the shaft 42 between the first end 52 and the second end 54 so as to contact the machine fluid 16 when the shaft 42 is positioned within the cavity 32 of the sight glass 18. Each of the plurality of indicators 44 may be configured to test for one or more contaminants in the machine fluid 16. In some embodiments, the plurality of indicators 44 may include a first indicator 44-1, a second indicator 44-2, and a third indicator 44-3. Although shown in FIGS. 2-5 as having three indicators, it should be understood by one skilled in the art that the probe 20 may have any number of indicators 44. As shown in FIGS. 3-5, the first indicator 44-1 of the plurality of indicators 44 may have at least a first indicator cross-sectional axis 86 which is smaller than the second cross-sectional axis 68 of the second portion 60 of the shaft 42, whereby the first indicator 44-1 may at least partially define a recess 88.

In some embodiments, the first indicator 44-1 may comprise a magnet positioned on the first portion 58 of the shaft 42. The magnet of the first indicator 44-1 may attract certain contaminants, such as ferrous particles, within the machine fluid 16. The first indicator 44-1 may thereby provide an indication of machine wear or other causes for the introduction of ferrous particles into the machine fluid 16. As the first indicator 44-1 contacts the machine fluid 16, ferrous particles may contact and adhere to the magnet of the first indicator 44-1 and collect in the recess 88. When the probe 20 is removed from contact with the machine fluid 16, at least a portion of the ferrous particles may remain in the recess 88 after removal of the probe 20 from the cavity 32 of the sight glass 18. Although shown in FIGS. 3-5 as a continuous magnet surrounding the first portion 58 of the shaft 42, it should be understood by one skilled in the art that the first indicator 44-1 may include a single magnet or a plurality of magnets in addition to other components. For example, in some embodiments, the first indicator 44-1 may be formed from a plastic member having one or a plurality of magnets connected thereto or otherwise positioned therein such that the one or plurality of magnets of the first indicator 44-1 may contact the machine fluid 16. Although the first indicator 44-1 is described as having a magnet that may attract certain contaminants, such as ferrous particles, within the machine fluid 16, it should be understood that the first indicator 44-1 does not have to solely include a magnet or provide an indication with respect to ferrous particles. Rather, the first indicator 44-1 may be any type of indicator in which what is being indicated (ferrous particles on magnet or corrosion on copper/steel) would not be wiped away by the at least one seal 22 when the probe 20 was removed from the machine fluid 16.

In some embodiments, the second indicator 44-2 may be formed from or at least in part comprise copper. As shown in FIGS. 1-5, the second indicator 44-2 may be formed as a copper band or washer capable of being positioned on the first portion 58 of the shaft 42. The copper of the second indicator 44-2 may react with certain contaminants, such as hydrogen sulphide, iron disulphide, sulphur dioxide, carbonyl sulphide, carbon disulphide, elemental sulphur, elemental sulphur and carbon monoxide, formic acid and acetic acid, water, or other contaminants, within the machine fluid 16. The second indicator 44-2 in the presence of certain types of contaminants may begin to show signs of patina or corrosion indicating the existence of one or more contaminants. When the probe 20 is removed from contact with the machine fluid 16, the removal of the probe 20 may strip away a negligible amount of corrosion on the surface of the second indicator 44-2 while maintaining enough corrosion to provide evidence of one or more contaminant within the machine fluid 16.

In some embodiments, the second indicator 44-2 may also include an indicator element 89, formed of copper, another substance, or a combination of substances, and an insulator 90. The insulator 90 may extend at least partially around the indicator element 89 such that the insulator 90 is positioned between the indicator element 89 and the first portion 58 of the shaft 42. In some embodiments, the insulator 90 may be a galvanic insulator. In some further embodiments, as shown in FIGS. 3-5, the galvanic insulator 90 may extend at least partially around the indicator element 89 such that the galvanic insulator 90 isolates the indicator element 89 from the first indicator 44-1 and the third indicator 44-3 to prevent galvanic corrosion or other types of corrosion from forming when the indicator element 89, the first indicator 44-1 and/or the third indicator 44-3 are made of dissimilar metals. The insulator 90 may be formed from rubber, plastic, or any other suitable insulating material. For example, the insulator 90, in some embodiments, may be formed from an insulating material positioned on one or more sidewalls 91 of the indicator element 89 and capable of preventing a galvanic reaction between the second indicator 44-2 and the first indicator 44-1, the third indicator 44-3, or the shaft 42.

In some embodiments, the third indicator 44-3 may be formed from steel. As shown in FIGS. 1-5, the third indicator 44-3 may be formed as a steel band or washer capable of being positioned on the first portion 58 of the shaft 42. The steel of the third indicator 44-3 may react with certain contaminants, such as water, within the machine fluid 16. The third indicator 44-3, in the presence of certain types of contaminants, may begin to show signs of patina or corrosion indicating the existence of one or more contaminants within the machine fluid 16. When the probe 20 is removed from contact with the machine fluid 16, the removal of the probe 20 may strip away a negligible amount of corrosion from the surface of the third indicator 44-3 while maintaining enough corrosion to provide evidence of the one or more contaminant.

The third indicator 44-3 may include an insulator 92 and an indicator element 93. The insulator 92 may be implemented similarly to the insulator 90. For example, the insulator 92 may be a galvanic insulator which is positioned between the indicator element 93 and the first portion 58 of the shaft 42. In some embodiments, the galvanic insulator 92 may extend at least partially around one or more sidewalls 95 of the indicator element 93 to isolate the indicator element 93 from the second indicator 44-2 and the shoulder 62 of the shaft 42. The insulator 92 may be formed from an insulating material, similar to the insulator 90, such as, rubber or plastic.

The at least one seal 22 may surround the bore 36 and extend into the bore 36 to engage the shaft 42 to substantially prevent the pressurized machine fluid 16 from exiting the bore 36. The at least one seal 22 may be formed from rubber, plastic, silicon, or any other suitable material capable of forming a seal between the sight glass 18 and the shaft 42. In some embodiments, the at least one seal 22 may include a first seal 22-1 and a second seal 22-2. The first seal 22-1 and the second seal 22-2 may be spaced a distance apart along the bore 36 with the first seal 22-1 surrounding the bore 36 and positioned proximate to the cavity 32. The second seal 22-2 may surround the bore 36 and be positioned proximate to the open second end 26 and the outside surface 34.

As shown in FIGS. 4 and 5, in embodiments having the first seal 22-1 and the second seal 22-2, the distance between the first seal 22-1 and the second seal 22-2 may be sufficient to maintain a seal on the shaft 42 regardless of the position of the recess 88 while removing the probe 20 from the cavity 32 of the sight glass 18. For example, as shown in FIG. 5, the probe 20 may initially be extended into the cavity 32 of the sight glass 18. The connection between the handle 40 and the sight glass 18 may be released, for example by unthreading the handle 40 from the sight glass 18. The shaft 42 may then be removed from the cavity 32. As the shaft 42 moves from a collapsed position, shown in FIG. 5, to an extended position, shown in FIG. 4, the first seal 22-1 and the second seal 22-2 are initially in contact with the spacer 72. When the first seal 22-1 encounters the recess 88, the first seal 22-1 may lose a sealing relationship with the shaft 42, while the second seal 22-2 maintains a sealing relationship with the shaft 42. Once the shaft 42 extends to a point where the recess 88 has passed the first seal 22-1, the first seal 22-1 may regain the sealing relationship with the shaft 42, contacting the second indicator 44-2, for example. As the shaft 42 continues to be removed from the cavity 32, the second seal 22-2 may lose the sealing relationship with the shaft 42 as the recess 88 passes through the second seal 22-2. At this point, when the second seal 22-2 loses the sealing relationship with the shaft 42, the first seal 22-1 maintains the sealing relationship. Once the recess 88 passes beyond the second seal 22-2, both the first seal 22-1 and the second seal 22-2 are in the sealing relationship with the shaft 42. In this manner, the first seal 22-1 and the second seal 22-2 enable at least partial removal of the shaft 42 from the cavity 32 while preventing the machine fluid 16 from exiting the bore 36.

In some embodiments, the coupling body 38 may have an open first end 94 and an open second end 96, an inside surface 98 and an outside surface 100 extending from the open first end 94 to the open second end 96 forming a coupling body cavity 102. In some embodiments, the coupling body 38 may be connected to the first end 24 of the sight glass 18. In these embodiments, the coupling body 38 may be removable from the sight glass 18 without destruction of the coupling body 38 or the sight glass 18. The coupling body 38 may be configured to be attached to the machine 14. In some embodiments, the coupling body 38 may be threaded proximate to the open first end 94 so as to be threaded into an opening in the machine 14. In some embodiments, the coupling body 38 may include a coupling body seal 104, such as an o-ring, proximate to the open first end 94 so as to enable a sealing relationship between the coupling body 38 and the machine 14.

In some embodiments, the coupling body 38 may connect to the sight glass 18 by receiving at least a portion of the open first end 24 of the sight glass 18 into the coupling body cavity 102. In these embodiments, the open first end 24 of the sight glass 18 may be inserted into the coupling body cavity 102 and contact an interior shoulder 106. After contacting the interior shoulder 106, the coupling body 38 and the sight glass 18 may form a sealing relationship, for example with a sight glass seal 108, such as an o-ring, encompassing at least a portion of the sight glass 18 proximate to the open first end 24 of the sight glass 18. The sight glass seal 108 may extend outwardly from the outside surface 34 of the sight glass 18 to contact the coupling body cavity 102. The sight glass seal 108 may be formed from rubber, silicon, plastic, or any other suitable material. In some embodiments, a locking ring 110 may be installed onto the coupling body 38 to secure the sight glass 18 to the coupling body 38.

The locking ring 110 may have an open first end 112, an open second end 114 opposite the open first end 112, a recess 116 extending from the open second end 114 toward the open first end 112, the recess 116 may define a locking ring shoulder 118 configured to contact at least a portion of the outside surface 34 of the sight glass 18 proximate to the open first end 24. A portion of the recess 116 may be internally threaded to cooperate with an externally threaded portion of the coupling body 38 proximate to the open second end 96.

In use, locking ring 110 may be placed over the sight glass 18 once the sight glass 18 is positioned within the coupling body cavity 102 and against the interior shoulder 106. Once the locking ring 110 has been placed over the sight glass 18, the locking ring 110 may be threaded onto the coupling body 38 so as to secure the sight glass 18 to the coupling body 38 using the locking ring shoulder 118 and the internally threaded portion of the locking ring 110.

Figure 6:
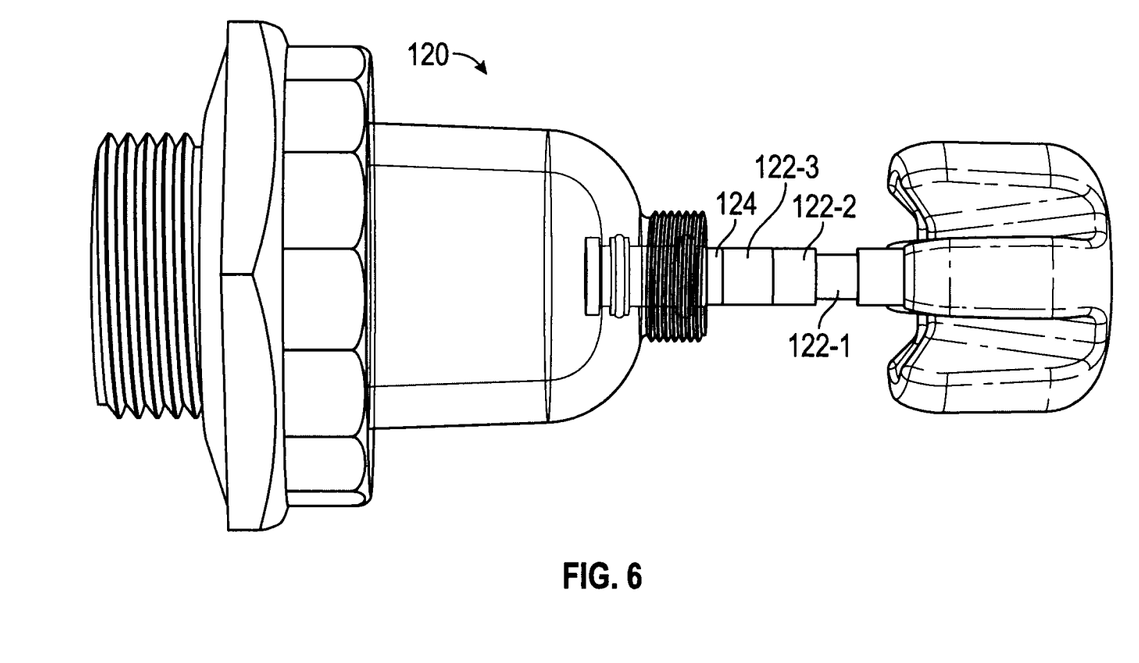
FIG. 6 is a side view of another version of a machine fluid testing assembly, in accordance with some embodiments of the present disclosure.

Referring now to FIG. 6, therein shown is a machine fluid testing assembly 120, implemented similarly to the machine fluid testing assembly 10. However, the machine fluid testing assembly 120 may include a first indicator 122-1, a second indicator 122-2, and a third indicator 122-3 positioned on a shaft 124, where the second indicator 122-2 and the third indicator 122-3 are not provided with insulators between the second and third indicators 122-2 and 122-3 and the shaft 124 or between the first, second, and third indicators 122-1, 122-2, and 122-3.

Figure 7:
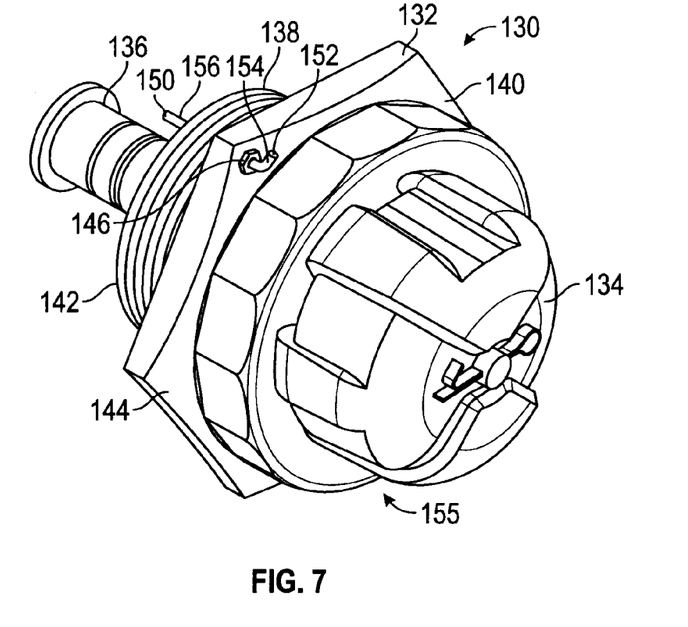
FIG. 7 is perspective view of another version of a machine fluid testing assembly with a machine fluid testing probe in a collapsed position, in accordance with some embodiments of the present disclosure.
Figure 8:
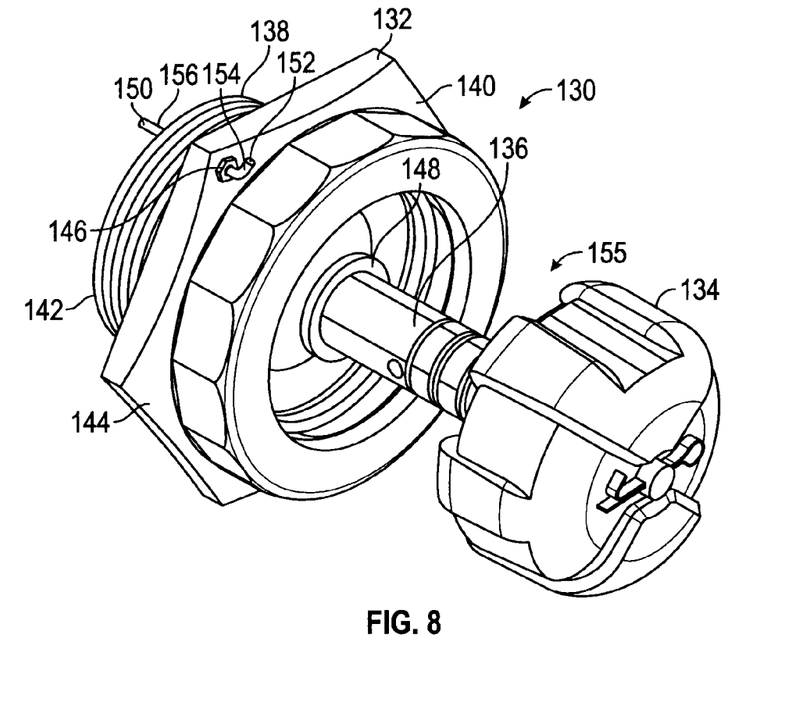
FIG. 8 is a perspective view of the machine fluid testing assembly of FIG. 7 with the machine fluid testing probe in an extended position.

Referring now to FIGS. 7 and 8, therein shown is a machine fluid testing assembly 130, in accordance with some embodiments of the present disclosure, in which a sight glass is absent. The machine fluid testing assembly 130 may include a coupling body 132, a handle 134, and a shaft 136 connected to the handle 134 and configured to be removably positioned within the coupling body 132. The coupling body 132 may be implemented similarly to the coupling body 38, with an open first end 138 and an open second end 140, an inside surface 142 and an outside surface 144 extending from the open first end 138 to the open second end 140 forming a coupling body cavity (similar to the bore 36) such that the shaft 136 is positionable within the coupling body cavity. The coupling body 132 may further have a sampling port assembly 146 extending from the coupling body cavity through the inside surface 142 and the outside surface 144. The coupling body 132 may further include at least one seal 148, and preferably two or more seals 148, surrounding the coupling body cavity and extending into the coupling body cavity to engage the shaft 136 to prevent the machine fluid 16 from exiting the coupling body cavity. The at least one seal 136 may be implemented similarly to the at least one seal 22, where the at least one seal includes a first seal and a second seal spaced a distance apart along the coupling body cavity to maintain a sealing relationship with the shaft 136 as the shaft 136 is removed from the coupling body cavity.

The sampling port assembly 146 may have a first end 150 and a second end 152, an inside surface (not shown) and an outside surface 154 from the first end 150 to the second end 152 forming a sealable access pathway whereby one or more samples of the machine fluid 16 are accessible. The sampling port assembly 146 may be positioned directly into the coupling body 132 such that the first end 150 of the sampling port assembly 146 extends through the open first end 138 of the coupling body 132 so as to contact the machine fluid 16. In some embodiments, the sampling port assembly 146 may include a valve to aid a user in drawing the machine fluid 16 out of the machine 14 through a pilot tube 156 and the sampling port assembly 146.

The handle 134 and shaft 136 may be connected together to form a probe 155 implemented similarly to the probe 20. The handle 134 may be implemented similarly to the handle 40. The shaft 136 may be implemented similarly to the shaft 42 or the shaft 124.

In some embodiments, the machine fluid testing assembly 10 may be used in a method. In some embodiments, the machine fluid testing assembly 10 may be connected to an opening of the machine 14 such that the shaft 42 of the machine fluid testing probe 20 may contact the machine fluid 16 when the machine 14 contains the machine fluid 16. After a period of operation, a user may at least partially remove the shaft 42 from contact with the machine fluid 16, while preventing the machine fluid 16 from escaping the machine 14. The plurality of indicators 44 may provide a visual indication of one or more contaminants within the machine fluid 16. The user may perform a visual inspection of the plurality of indicators 44 to determine whether one or more contaminants are present within the machine fluid 16. Where the plurality of indicators 44 indicate contaminants, the user may replace one or more of the plurality of indicators and re-establish contact between the machine fluid 16 and the shaft 42 of the machine fluid testing probe 20.

In some embodiments, one or more of the plurality of indicators 44 may be replaced on the shaft 42 of the machine fluid testing probe 20. To replace one or more of the plurality of indicators 44, the user may at least partially remove the shaft 42 from contact with the machine fluid 16 while preventing escape of the machine fluid 16. The user may remove the handle 40 from the releasable connection between the handle 40 and the shaft 42. The user may remove the spacer 72 and one or more of the plurality of indicators 44 from the shaft 42. The user may then position one or more plurality of indicators 44, which are new or cleaned, onto the shaft 42 and replace the spacer 72. The user may then reconnect the handle 40 to the shaft 42 and re-establish contact between the machine fluid 16 and the shaft 42 of the machine fluid testing probe 20.

Although the preceding description has been described herein with reference to particular means, materials and embodiments, it is not intended to be limited to the particulars disclosed herein; rather, it extends to functionally equivalent structures, methods, and uses, such as are within the scope of the appended claims.

What is claimed is:

1. A machine fluid testing probe, comprising:
   a handle;
   a shaft connected to the handle and extending outwardly from handle, the shaft having a first end proximate to the handle, a second end opposite the first end, and a length extending between the first end and the second end, a first portion extending from the first end toward the second end, a second portion extending from the first portion toward the second end, and a shoulder defined by the second portion of the shaft at an intersection of the first portion and the second portion, the first portion having a first cross-sectional axis, the second portion having a continuous arcuate external surface having a second cross-sectional axis greater than the first cross-sectional axis and extending across the continuous arcuate external surface, wherein the shaft is configured to be removably positioned to contact a machine fluid of a machine; and
   a plurality of indicators supported by the first portion of the shaft between the first end and the second end so as to contact the machine fluid, each of the plurality of indicators configured to test for one or more contaminants in the machine fluid, wherein a first indicator of the plurality of indicators has at least a first indicator cross-sectional axis which is smaller than the second cross-sectional axis of the second portion of the shaft whereby the first indicator at least partially defines a recess.

2. The machine fluid testing probe of claim 1, wherein the handle has a first end and a second end, the second end forming a recess extending inwardly toward the first end.

3. The machine fluid testing probe of claim 1, wherein the shaft further comprises a third portion between the second end and the second portion, the third portion forming a stop member extending outwardly relative to the continuous arcuate external surface of the second portion.

4. The machine fluid testing probe of claim 1, further comprising a spacer supported by the first portion of the shaft and positioned between the plurality of indicators and the handle, the spacer having a cross-sectional axis equal to the second cross-sectional axis of the second portion of the shaft.

5. The machine fluid testing probe of claim 1, wherein the plurality of indicators comprises the first indicator, a second indicator, and a third indicator.

6. The machine fluid testing probe of claim 5, wherein the first indicator comprises at least one of a magnet configured to attract ferrous particles, and a non-magnetic material configured to detect a property within the machine fluid other than ferrous particles.

7. The machine fluid testing probe of claim 5, wherein the second indicator is formed from copper.

8. The machine fluid testing probe of claim 5, wherein the second indicator further comprises an indicator element made of a material dissimilar to the first indicator, and an insulator extending at least partially around one or more sidewalls of the indicator element to prevent galvanic corrosion.

9. The machine fluid testing probe of claim 5, wherein the third indicator is formed from steel.

10. The machine fluid testing probe of claim 5, wherein the third indicator further comprises an indicator element made of a material dissimilar to the first indicator, and an insulator extending at least partially around one or more sidewalls of the indicator element to prevent galvanic corrosion.

11. The machine fluid testing probe of claim 1, wherein the plurality of indicators are removably positioned on the second portion of the shaft without destruction of the indicators or the shaft.

12. The machine fluid testing probe of claim 1, wherein the shaft is removably connected to the handle without destruction of the shaft or the handle.

13. The machine fluid testing probe of claim 12, wherein the first portion of the shaft defines a hole proximate to the first end of the shaft, the hole configured to receive a cotter pin to secure the handle to the shaft.

14. A machine fluid testing assembly, comprising:
a handle;
a shaft connected to the handle and extending outwardly from the handle, the shaft having a first end proximate to the handle, a second end opposite the first end, and a length extending between the first end and the second end, a first portion extending from the first end toward the second end, a second portion extending from the first portion toward the second end, and a shoulder defined by the second portion of the shaft at an intersection of the first portion and the second portion, the first portion having a first cross-sectional axis, the second portion having a continuous arcuate external surface having a second cross-sectional axis greater than the first cross-sectional axis and extending across the continuous arcuate external surface, wherein the shaft is configured to be removably positioned to contact a machine fluid of a machine;
a plurality of indicators supported by the first portion of the shaft between the first end and the second end so as to contact the machine fluid, each of the plurality of indicators configured to test for one or more contaminants in the machine fluid, wherein a first indicator of the plurality of indicators has at least a first indicator cross-sectional axis which is smaller than the second cross-sectional axis of the second portion of the shaft whereby the first indicator at least partially defines a recess; and
a coupling body having an open first end and an open second end, an inside surface and an outside surface extending from the open first end to the open second end forming a coupling body cavity such that the shaft is positionable within the coupling body cavity, the coupling body further having a port extending from the coupling body cavity through the inside surface and the outside surface.

15. The machine fluid testing assembly of claim 14, further comprising a spacer supported by the first portion of the shaft and positioned between the plurality of indicators and the handle, the spacer having a cross-sectional axis equal to second cross-sectional axis of the second portion of the shaft.

16. The machine fluid testing assembly of claim 14, wherein the plurality of indicators comprises a first indicator, a second indicator, and a third indicator.

17. The machine fluid testing assembly of claim 16, wherein the first indicator comprises a magnet.

18. The machine fluid testing assembly of claim 16, wherein the second indicator is formed from copper.

19. The machine fluid testing assembly of claim 16, wherein the second indicator further comprises an indicator element made of a material dissimilar to the first indicator and an insulator extending at least partially around one or more sidewalls of the indicator element to prevent galvanic corrosion.

20. The machine fluid testing assembly of claim 16, wherein the third indicator is formed from steel.

21. The machine fluid testing assembly of claim 16, wherein the third indicator further comprises an indicator element made of a material dissimilar to the first indicator and an insulator extending at least partially around one or more sidewalls of the indicator element to prevent galvanic corrosion.

22. The machine fluid testing assembly of claim 14, wherein the plurality of indicators are removably positioned on the shaft without destruction of the plurality of indicators or the shaft.

23. The machine fluid testing assembly of claim 14, wherein the shaft is removably connected to the handle without destruction of the shaft or the handle.

24. The machine fluid testing assembly of claim 23, wherein the first portion of the shaft defines a hole proximate to the first end of the shaft, the hole configured to receive a cotter pin to secure the handle to the shaft.

25. A machine fluid testing assembly, comprising:
a sight glass at least partially constructed of one or more material that is transparent to light in a visible region, the sight glass configured to be attachable to a machine such that machine fluid is viewable through the sight glass, the sight glass having an inside surface surrounding a cavity, an outside surface, and a bore extending from the inside surface to the outside surface;
a probe extending through the bore of the sight glass such that at least a portion of the probe is positionable for contact with the machine fluid, the probe having a handle, a shaft extending outwardly from the handle, a stop member connected to the shaft, and a plurality of indicators positioned on the shaft, the shaft having a first end proximate to the handle, a second end opposite the first end, and a length extending between the first end and the second end, the shaft configured to be removably extended into the cavity to contact a machine fluid within the cavity, the stop member connected to the shaft, proximate to the second end and extending outwardly from the shaft to prevent removal from the cavity, and the plurality of indicators positioned on the shaft to contact the machine fluid and configured to test for one or more contaminants within the machine fluid; and at least one seal surrounding the bore and extending into the bore to engage the shaft to prevent the machine fluid from exiting the bore.

26. The machine fluid testing assembly of claim 25, wherein the sight glass has an open first end and an open second end, and wherein the open second end defines the bore, wherein the open first end of the sight glass is configured to be attachable to the machine such that the machine fluid is transferrable from the machine to the sight glass.

27. The machine fluid testing assembly of claim 26, wherein the at least one seal is a first seal and a second seal, the first seal and the second seal being spaced a distance apart along the bore with the first seal surrounding the bore and positioned proximate to the cavity of the sight glass and the second seal surrounding the bore and positioned proximate to the open second end and the outside surface.

28. The machine fluid testing assembly of claim 26, further comprising a coupling body connected to the open first end of the sight glass and removable from the sight glass without destruction of the coupling body or the sight glass, the coupling body configured to be attached to the machine.

29. The machine fluid testing assembly of claim 25, wherein the plurality of indicators comprises a first indicator, a second indicator, and a third indicator.

30. The machine fluid testing assembly of claim 29, wherein the first indicator comprises a magnet.

31. The machine fluid testing assembly of claim 29, wherein the second indicator is formed from copper.

32. The machine fluid testing assembly of claim 29, wherein the second indicator further comprises an indicator element made of a material dissimilar to the first indicator, and an insulator extending at least partially around one or more sidewalls of the indicator element to prevent galvanic corrosion.

33. The machine fluid testing assembly of claim 29, wherein the third indicator is formed from steel.

34. The machine fluid testing assembly of claim 29, wherein the third indicator further comprises an indicator element made of a material dissimilar to the first indicator, and an insulator extending at least partially around one or more sidewalls of the indicator element to prevent galvanic corrosion.

35. The machine fluid testing assembly of claim 25, wherein the plurality of indicators are removably positioned on the shaft.

36. The machine fluid testing assembly of claim 25, wherein the shaft is releasably connected to the handle.

* * * * *